(12) United States Patent
Chen et al.

(10) Patent No.: US 7,141,723 B2
(45) Date of Patent: Nov. 28, 2006

(54) **TRANSGENIC PLANTS RESISTANT TO *SCLEROTINIA* AND *PHOMA LINGAM***

(75) Inventors: Zhizheng Chen, Fort Collins, CO (US); Sonia Hallier, Livermore, CO (US); Xinmin Deng, Camrose (CA)

(73) Assignee: Cargill, Incorporated, Wayzata, MN (US)

( * ) Notice: Subject to any disclaimer, the term of this patent is extended or adjusted under 35 U.S.C. 154(b) by 123 days.

(21) Appl. No.: 10/470,427

(22) PCT Filed: Jan. 29, 2002

(86) PCT No.: PCT/US02/02444

§ 371 (c)(1),
(2), (4) Date: Dec. 15, 2003

(87) PCT Pub. No.: WO02/061043

PCT Pub. Date: Aug. 8, 2002

(65) Prior Publication Data

US 2004/0093640 A1    May 13, 2004

Related U.S. Application Data

(60) Provisional application No. 60/264,776, filed on Jan. 29, 2001.

(51) Int. Cl.
*A01H 5/00* (2006.01)
*C12N 15/82* (2006.01)

(52) U.S. Cl. .................. 800/301; 800/279; 800/306; 800/312; 800/322; 800/317.4

(58) Field of Classification Search .............. None
See application file for complete search history.

(56) References Cited

U.S. PATENT DOCUMENTS

| | | |
|---|---|---|
| 5,188,958 A | 2/1993 | Moloney et al. |
| 5,204,253 A | 4/1993 | Sanford et al. |
| 5,389,609 A | 2/1995 | Woloshuk et al. |
| 5,451,513 A | 9/1995 | Maliga et al. |
| 5,501,967 A | 3/1996 | Offringa et al. |
| 5,530,187 A | 6/1996 | Lamb et al. |
| 5,670,706 A | 9/1997 | Cornelissen et al. |
| 5,856,151 A | 1/1999 | Woloshuk et al. |
| 5,866,776 A | 2/1999 | Marie de Wit |
| 5,877,402 A | 3/1999 | Maliga et al. |
| 5,993,808 A | 11/1999 | Melchers et al. |
| 5,994,625 A | 11/1999 | Melchers et al. |
| 6,066,491 A | 5/2000 | Cornelissen et al. |
| 6,087,161 A | 7/2000 | Cornelissen et al. |
| 6,087,560 A | 7/2000 | Cornelissen et al. |

FOREIGN PATENT DOCUMENTS

| | | |
|---|---|---|
| EP | 460 753 A2 | 12/1991 |
| EP | 460 753 A3 | 12/1991 |
| EP | 1 041 148 | 10/2000 |
| WO | 92/17591 | 10/1992 |
| WO | 94/08009 | 4/1994 |
| WO | 95/21929 | 8/1995 |
| WO | 97/16973 | 5/1997 |
| WO | 97/32973 | 9/1997 |
| WO | WO 97/37024 | 10/1997 |
| WO | 98/13478 | 4/1998 |
| WO | 98/49331 | 11/1998 |
| WO | WO 98/49331 | 11/1998 |
| WO | 99/43202 | 9/1999 |
| WO | 99/45129 | 9/1999 |
| WO | 99/50423 | 10/1999 |
| WO | 99/50428 | 10/1999 |
| WO | 00/07430 | 2/2000 |
| WO | WO 00/11175 | 3/2000 |

OTHER PUBLICATIONS

Jach et al., "Enhanced Quantitative Resistance Against Fungal Disease by Combinatorial Expression of Different Barley Antifungal Proteins in Transgenic Tobacco," *Plant Journal*, 1995, 8(1):97-109.

Lorito et al., "Synergistic Interaction Between Cell Wall Degrading Enzymes and Membrane Affecting Compounds," *Molecular Plant-Microbe Interactions*, 1996, 9(3):206-213.

Melchers et al., "Novel genes for disease-resistance breeding," *Current Opinion in Plant Biology*, 2000, 3(2):147-152.

Alexander et al., "Increased tolerance to two oomycete pathogens in transgenic tobacco expressing pathogenesis-related protein 1a," 1993, *Proc. Natl. Acad. Sci. USA*, 90:7327-7331.

Grison et al., "Field tolerance to fungal pathogens of *Brassica napus* constitutively expressing a chimeric chitinase gene," 1996, *Nature Biotechnology*, 14:643-646.

Pontier et al., "*hsr203J*, a tobacco gene whose activation is rapid, highly localized and specific for incompatible plant/pathogen interactions," *Plant J.*, 1994, 5:507-521.

Radke et al., "Transformation and regeneration of *Brassica rapa* using *Agrobacterium tumefaciens*," *Plant Cell Reports*, 1992, 11:499-505.

Walkerpeach and Velten, "*Agrobacterium*-mediated gene transfer to plant cells: cointegrate and binary vector systems," *Plant Molecular Biology Manual*, 1994, B1:1-19.

Weising et al., "Foreign Genes in Plants: Transfer, Structure, Expression, and Applications," *Annu. Rev. Genet.*, 1988, 22:421-477.

Williams and Delwiche, "Screening for Resistance to Blackleg of Crucifers in the Seedling Stage," *Proceedings of a EUCARPIA-conference on the breeding of Cruciferous crops*, Oct. 1-3, 1979, p. 164.

Zhu et al., "Enhanced Protection Against Fungal Attack by Constitutive Co-expression of Chitinase and Glucanase Genes in Transgenic Tobacco," *Bio/Technology*, 1994, 12:807-812.

*Primary Examiner*—Anne Kubelik
(74) *Attorney, Agent, or Firm*—Fish & Richardson P.C.

(57) ABSTRACT

Transgenic plants that are resistant to *Sclerotinia* or *Phoma lingam* are described as well as methods for producing such tranagenic plants. The transgenic plants include nucleic acid constructs that encode a chitinase polypeptide, a β-1,3-glucanase polypeptide, an osmotin polypeptide, and a pathogenesis-related-1 polypeptide.

27 Claims, 3 Drawing Sheets

TRANSGENIC PLANTS RESISTANT TO SCLEROTINIA AND PHOMA LINGAM

CROSS REFERENCE TO RELATED APPLICATIONS

Figure 1:
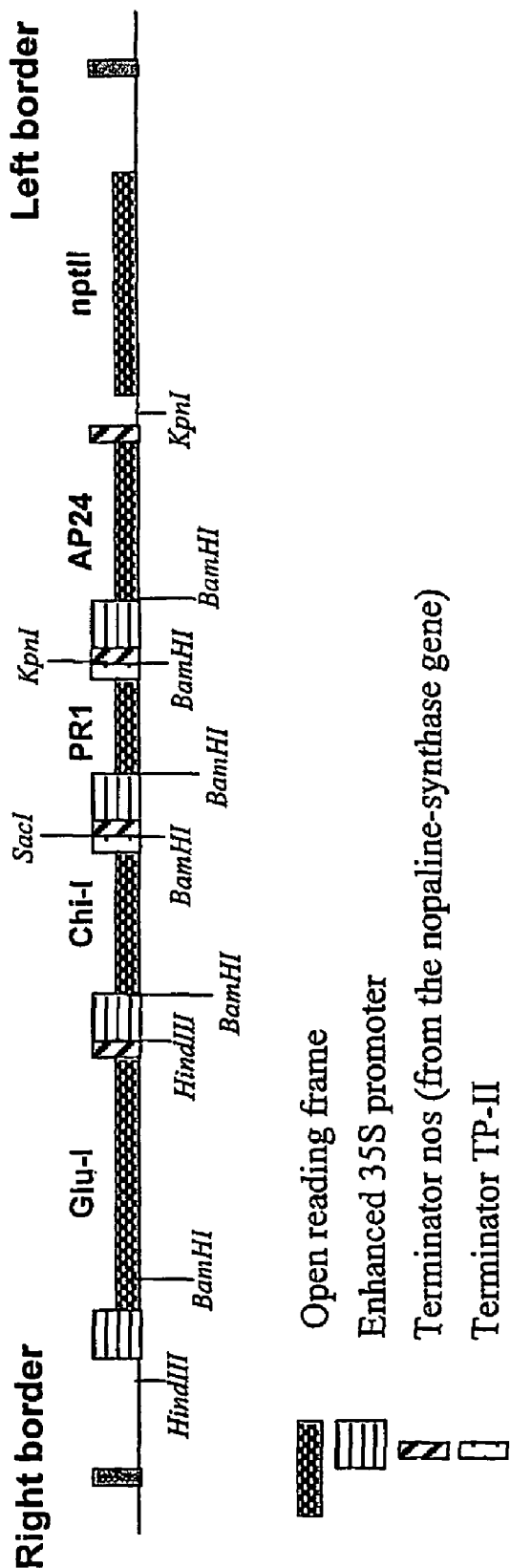

This application is a National Stage Application under 35 U.S.C. §371 that claims the benefit of application Ser. No. PCT/US02/02444, filed Jan. 29, 2002, now pending, which claims the benefit of U.S. Provisional Application Ser. Nos. 60/264,776, filed Jan. 29, 2001, now expired.

TECHNICAL FIELD

This invention relates to fungal resistance in plants and, more particularly, to plants resistant to *Sclerotinia sclerotiorum* and/or *Phoma lingam* infections.

BACKGROUND

Fungal diseases are responsible for damage to many cultivated species. The amount of damage varies each year, depending on temperature, amount of rain, and quantity of inoculum present in fields. In some instances, fungal diseases can completely destroy fields, leading to an estimated average loss of yield of 20% on crops worldwide. Blackleg, one of the predominant fungal diseases in rape plants, typically results in losses of tens of millions of dollars annually. *Sclerotinia*, another predominant fungal disease of Cruciferae plants, which includes *Brassica* plants, as well as 400 other species of plants, including Compositae plants such as sunflower and leguminous plants such as pea, also can result in significant economic losses.

Blackleg disease is caused by an Ascomycetes fungus whose perfect or sexual form is *Leptosphaeria maculans* and whose imperfect or asexual form is *Phoma lingam*. The sexual form provides the primary inoculum each year and is responsible for the high variability of the fungus. *L. maculans* is in fact a complex of species, of which two main groups have been identified, TOX$^+$ and TOX$^\circ$. The TOX$^+$ species is aggressive and produces two toxins, sirodesmin and phomalide. Within the TOX$^+$ species, several strains or pathogenicity groups (PG) exist. In Europe, Australia, and Eastern Canada, PG3 and PG4 currently are the predominant strains of *Phoma*, while in Western Canada, PG2 currently is the predominate strain of *Phoma*. Damage to rape plants in Europe is typically limited to attack of the crown, but in North America, necrosis can occur both on the crown and the stem.

White rot or *sclerotinia* disease also is caused by an Ascomycetes fungus, *Sclerotinia sclerotiorum*. *S. sclerotiorum* is the sexual form of the fungus and provides the primary inoculum each year.

Strategies for limiting fungal damage include prophylactic measures such as crop rotations or burying of crop debris, fungicide use, and genetic improvement. Prophylactic measures, however, are not very effective as the fungus can survive for many years in the soil. Fungicides can be effective when applied at the appropriate time, but cost often is high compared with any gain in yield. Furthermore, genetic improvement in plants for resistance to *S. sclerotiorum* has been limited as only low tolerance to the fungus exists in various plant species. Varieties of rape plants that are tolerant to the PG3 strain of *L. maculans*, which contain a single resistance gene, have lost efficacy due to adaptation of the fungus or dilution of the tolerance factors in new rape plant genotypes. Thus, a need exists for plants that are resistant to such fungi as well as for methods of improving plant resistance to fungi.

SUMMARY

The invention is based on the discovery that expressing certain combinations of proteins provides plants with the ability to resist infections of *P. Lingam* and/or *S. sclerotiorum*. In particular, expressing two or more proteins such as chitinase, glucanase, osmotin, and pathogenesis-related protein 1 (PR1), provides resistance that is enhanced compared with existing natural resistance. Expression of the proteins can be manipulated such that the proteins are expressed at particular locations (e.g., the stem), at a particular stage of development, or upon stimulation by the appropriate environmental conditions. Furthermore, expressing combinations of proteins results in a polygenic resistance that can prolong the period of efficacy of the resistance.

In one aspect, the invention features a transgenic plant that includes at least one nucleic acid construct, wherein the transgenic plant is resistant to *Sclerotinia* relative to a corresponding control plant. The plant can be a Cruciferae plant such as a plant selected from the group consisting of *Brassica napus*, *Brassica juncea*, *Brassica nigra*, *Brassica oleracae*, *Brassica carinata* and *Brassica rapa*, or *Helianthus annuus*.

The nucleic acid construct includes a) a regulatory element operably linked to a nucleic acid encoding a chitinase polypeptide; b) a regulatory element operably linked to a nucleic acid encoding a β-1,3-glucanase polypeptide; and c) a regulatory element operably linked to a nucleic acid encoding an osmotin polypeptide. The nucleic acid construct further can include a regulatory element operably linked to a nucleic acid encoding a pathogenesis-related-1 (PR1) polypeptide. The PR1 polypeptide can be intracellularly expressed and can be from tobacco, parsley, *Brassica napus*, or *Arabidopsis thaliana*. The chitinase polypeptide can be from tobacco, bean, cucumber, tomato, *Arabidopsis thaliana*, or bacteria, and can be intracellularly expressed. The β-1,3-glucanase polypeptide can be from pea, soybean, tobacco, bean, rice, cucumber, or tomato, and can be intracellularly expressed. The osmotin polypeptide can be from tobacco, soybean, carrot, cotton, potato, or bean.

The transgenic plant can include three nucleic acid constructs, wherein each construct includes a regulatory element operably linked to a nucleic acid encoding one of the polypeptides. Chitinase, β-1,3-glucanase, and osmotin polypeptides can be constitutively expressed in the stem or leaves of the transgenic plant. The transgenic plant can be resistant to *Sclerotinia* on the stem or on the leaves.

In another aspect, the invention features a transgenic *Brassica* plant that includes at least one nucleic acid construct and wherein the plant is resistant to *Phoma lingam* relative to a corresponding control plant. The nucleic acid construct includes a) a regulatory element operably linked to a nucleic acid encoding an osmotin polypeptide; and b) a regulatory element operably linked to a nucleic acid encoding a chitinase polypeptide. The cotyledon and/or the stem of the transgenic plant can be resistant to *Phoma lingam*. The transgenic plant can be resistant to a PG2 or a PG3 strain of *Phoma lingam*.

The invention also features a method of producing a *Brassica* plant line resistant to *Phoma lingam*. The method includes a) introducing at least one nucleic acid construct into cells of a *Brassica* species (e.g., *B. napus*, *B. rapa*, *B. juncea*, *B. nigra*, *B. oleracea*, or *B. carinata*) that is susceptible to *Phoma lingam*, wherein the nucleic acid construct includes i) a regulatory element operably linked to a nucleic acid encoding an osmotin polypeptide; and ii) a regulatory element operably linked to a nucleic acid encoding a chitinase polypeptide; b) obtaining one or more progeny plants from the cells; c) identifying at least one of the progeny plants that is resistant to *Phoma lingam*; and d) producing the plant line from at least one progeny plant by self- or cross-pollination, wherein the plant line is resistant to *Phoma lingam*. The nucleic acid construct further can include a regulatory element operably linked to a nucleic acid encoding a β-1,3-glucanase polypeptide. The nucleic acid construct also can include a regulatory element operably linked to a nucleic acid encoding a PR1 polypeptide.

In another aspect, the invention features a method of producing a plant line resistant to *S. sclerotiorum*. The method includes a) introducing at least one nucleic acid construct into cells of a plant species that is susceptible to *S. sclerotiorum*, wherein the nucleic acid construct includes i) a regulatory element operably linked to a nucleic acid encoding a chitinase polypeptide; ii) a regulatory element operably linked to a nucleic acid encoding a β-1,3-glucanase polypeptide; and iii) a regulatory element operably linked to a nucleic acid encoding an osmotin polypeptide; b) obtaining one or more progeny plants from the cells; c) identifying at least one of the progeny plants that is resistant to *S. sclerotiorum*; and d) producing the plant line from the at least one progeny plant by self- or cross-pollination, wherein the plant line is resistant to *S. sclerotiorum*. The plant species that is susceptible to *S. sclerotiorum* can be a Cruciferae species such as a *Brassica* species, soybean, *Helianthus annuus*, or tomato. The nucleic acid construct further can include a regulatory element operably linked to a nucleic acid encoding a PR1 polypeptide.

The invention also features a nucleic acid construct that includes a) a regulatory element operably linked to a nucleic acid encoding a chitinase polypeptide; b) a regulatory element operably linked to a nucleic acid encoding a β-1,3-glucanase polypeptide; and c) a regulatory element operably linked to a nucleic acid encoding an osmotin polypeptide. The nucleic acid construct further can include a regulatory element operably linked to a nucleic acid encoding a PR1 polypeptide. The chitinase polypeptide can be from tobacco, bean, cucumber, or tomato, and can be intracellularly expressed. The β-1,3-glucanase polypeptide can be from pea, soybean, tobacco, bean, cucumber, or, tomato, and can be intracellularly expressed. The osmotin polypeptide can be from tobacco, soybean, carrot, cotton, potato, or bean. The regulatory element can be an enhanced 35S promoter from cauliflower mosaic virus.

In yet another aspect, the invention features a nucleic acid construct that includes: a) a regulatory element operably linked to a nucleic acid encoding an osmotin polypeptide; and b) a regulatory element operably linked to a nucleic acid encoding a chitinase polypeptide. Such a nucleic acid construct can further include a regulatory element operably linked to a nucleic acid encoding a β-1,3-glucanase polypeptide and/or a regulatory element operably linked to a nucleic acid encoding a PR1 polypeptide.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1 is a schematic of pMOG803.

FIG. 2 is a schematic of selecting and screening steps used for identifying transgenic lines.

FIG. 3 is a graph of the correlation between chitinase expression and glucanase expression ($R^2$=0.6) in leaves. Expression values for chitinase and glucanase are both relative to line 213.

DETAILED DESCRIPTION

The invention features transgenic plants that are resistant to fungi, in particular, to *Sclerotinia sclerotiorum* and *Phoma lingam*, and methods of making such plants. Transgenic plants and plant lines of the invention express combinations of proteins that are involved in host defense, such as two or more of a chitinase, β-1,3-glucanase, osmotin or osmotin-like (e.g., AP24), and PR1. Other host defense proteins that can be used in combination with chitinase, β-1,3-glucanase, osmotin, or PR1 include peroxidases, ribosome inactivating proteins, protease inhibitors, defensins, thionins, ribonucleases, polygalacturonase inhibitor proteins, lipid transfer proteins, glycine-rich proteins, and extensin or hydroxyproline rich proteins.

Chitinases are endohydrolases that hydrolyze the β-1,4 bond between the N-acetylglucosmine residues of chitin, a component of the wall of many pathogenic fungi. Chitinases are divided into four classes based on primary structure. Class I chitinases contain a cysteine rich domain that is approximately 40 amino acids in length. Class II chitinases are similar to the Class I chitinases based on amino acid sequence homology, but do not contain the cysteine rich domain. Both class I and class II chitinases have a monomeric catalytic domain. Class III chitinases do not share homology with class I or II chitinases. Class IV chitinases have homology to the class I chitinases and contain a cysteine rich domain, but are smaller than class I chitinases. Class IV chitinases include the sugar beet chitinase, the basic rape chitinase ChB4, and the acidic bean PR4 chitinase. Chitinases that are suitable for use in the invention have been cloned from *Arabidopsis*, tobacco, bean, cucumber, tomato, and bacteria. Tobacco chitinase is particularly useful. Typically, intracellularly expressed chitinases are used to provide fungal resistance, although in some embodiments, extracellularly expressed chitinases can be used. The nucleic acid and amino acid sequences of a suitable intracellular tobacco chitinase are provided under GenBank Accession No. A16119. Other suitable chitinases can be found under GenBank Accession No. AB015996 for chiA of *Serratia marcescens*, GenBank Accession No. AB026636 for an *Arabidopsis thaliana* chitinase, and GenBank Accession No. AJ301671 for a *Nicotinia sylvestris* endochitinase. See also, U.S. Pat. No. 5,993,808.

β-1,3-glucanases are a family of endohydrolases that degrade fragments of glucan, another component of the wall of pathogenic fungi. Glucanases are part of the PR3 family, and are grouped into three classes. Class I glucanases have a molecular weight of approximately 33 kD at the mature stage and, generally, are located in the vacuole. Class II and III glucanases generally are extracellular and have molecular weights ranging from about 34 to 36 kD. Suitable β-1,3-glucanases have been cloned from *Arabidopsis*, pea, soybean, tobacco, bean, cucumber, tomato, rice, *Hevea* (para rubber), and bacteria, with tobacco β-1,3-glucanase being particularly useful in the invention. As with chitinases, intracellularly expressed β-1,3-glucanases typically are used to provide fungal resistance, although in some embodiments, extracellularly expressed glucanases can be used. The nucleic acid and amino acid sequences of a suitable intracellular β-1,3-glucanase from tobacco are provided under GenBank Accession No. A16121. Also see GenBank Accession Nos. AB025632, AL353822, and D76437 for the nucleic acid and amino acid sequences of glucanases from *A. thaliana, Neurospora crassa*, and rice, respectively. See also, U.S. Pat. Nos. 6,087,560 and 6,066,491.

PR5 proteins are thaumatin-like proteins that are part of the osmotin family of proteins. Osmotins have an external surface with highly basic residues. Osmotins are thought to permeabilize the membrane surface of fungi, resulting in a modification of the pH gradient and destabilization of pressure gradients that maintain the tip of the hyphae in a tensed state. Consequently, cytoplasmic material is leaked and the hyphae rupture, or in the case of spores, the spores lyse. Suitable osmotin or osmotin-like polypeptides have been cloned from tobacco, soybean, carrot, cotton, potato, and bean. AP24 is a basic osmotin that is normally stored in the vacuole like class I chitinases and glucanases, and is useful in the invention. Endogenous AP24 typically is expressed intracellularly, although in some embodiments, extracellular AP24 can be used. Tobacco AP24 is particularly useful. The nucleic acid and amino acid sequences of a suitable intracellular AP24 from tobacco are provided under GenBank Accession No. X65701. GenBank Accession Nos. M29279, AL049500, and D76437 provide the nucleic acid and amino acid sequences of other osmotin or osmotin-like proteins from tobacco, *A. thaliana*, and *Nicotiana sylvestris*. See also, U.S. Pat. No. 6,087,161.

Endogenous PR1 proteins are highly induced during infection with pathogenic agents. PR1 proteins have a molecular weight of approximately 15 to 17 kD and are predominantly acidic. PR1 proteins contain a hydrophobic N-terminal sequence of 30 amino acids, which is thought to correspond with a signal peptide for translocation to the endoplasmic reticulum. Suitable PR1 proteins have been cloned from tobacco, *Arabidopsis*, and parsley. A basic PR1 protein that is expressed intracellularly is particularly useful in the invention. See, GenBank Accession No. X14065 for the nucleotide and amino acid sequences of this basic PR1 protein. Also see GenBank Accession Nos. AL031394, X12572, and AI352904 for the nucleic acid and amino acid sequences of PR1 proteins from *A. thaliana*, parsley, and *B. napus*, respectively.

Expressing combinations of chitinase, β-1,3-glucanase, osmotin (e.g., AP24), and PR1 provides resistance to *sclerotinia* and/or blackleg in transgenic plants of the invention. For example, expressing AP24 and chitinase in *Brassica* provides enhanced resistance to blackleg relative to a control plant that does not express the exogenous polypeptides. Expressing chitinase, glucanase, and AP24 provides enhanced resistance to *S. sclerotiorum* relative to a control plant that does not express the exogenous polypeptides. In some embodiments, two or more chitinases can be expressed with AP24 or in combination with AP24 and glucanase. For example, a barley class II chitinase and a tobacco class I chitinase can be expressed in combination with other host defense polypeptides. Two or more glucanases also can be expressed in combination with other host defense polypeptides. For example, class I and class II glucanases can be expressed in combination with other host defense polypeptides.

Nucleic Acid Constructs

Nucleic acid constructs suitable for producing transgenic plants of the invention include nucleic acids encoding host defense polypeptides operably linked to one or more regulatory elements such as a promoter. As used herein, the term "polypeptide" includes any chain of amino acids, regardless of length or post-translational modification, that retains the function of the enzyme. For example, chitinase polypeptides that are not full-length are within the scope of the invention if the chitinase polypeptide retains the ability to hydrolyze the β-1,4 bond between the N-acetylglucosamine residues of chitin. Each nucleic acid encoding a host defense polypeptide is operably linked to the regulatory elements in sense orientation. Standard molecular biology techniques can be used to generate nucleic acid constructs.

Regulatory elements typically do not themselves code for a gene product. Instead, regulatory elements affect the expression level of the coding sequence. Suitable promoters can be constitutive or inducible, and can be tissue specific (e.g., roots, seeds, veins, or the like) or developmental stage specific (e.g., *Brassica* developmental stages 1, 2, 3, 4, or 5). As used herein, "constitutive promoter" refers to a promoter that facilitates expression of a nucleic acid molecule without significant tissue- or temporal-specificity. An inducible promoter may be considered to be a "constitutive promoter," provided that once induced, expression of the nucleic acid molecule is relatively constant or uniform without significant tissue- or temporal-specificity. Suitable promoters are known (e.g., Weising et al., *Ann. Rev. Genetics* 22:421–478 (1988)). The following are representative examples of promoters suitable for use herein: regulatory sequences from fatty acid desaturase genes (e.g., *Brassica* fad2D or fad2F, see WO 00/07430); alcohol dehydrogenase promoter from corn; light inducible promoters such as the ribulose bisphosphate carboxylase (Rubisco) small subunit gene promoters from a variety of species; major chlorophyll a/b binding protein gene promoters; the 19S or 35S promoters of cauliflower mosaic virus (CaMV); hsr203j promoter from tobacco (Pontier et al., *Plant J.* 5: 507–21 (1994)) as well as synthetic or other natural promoters that are either inducible or constitutive. See, e.g., U.S. Pat. No. 6,087,560.

In some embodiments, the regulatory element is a promoter of plastid gene expression. Non-limiting examples of such a promoter include the 16S ribosomal RNA operon promoter, promoters of the photosynthetic genes rbcL and psbA, as well as the light-regulated promoter of the psbD operon. See, U.S. Pat. No. 5,877,402 for constructs suitable for stable transformation of plastids.

In other embodiments, regulatory sequences are seed-specific, i.e., the particular gene product is preferentially expressed in developing seeds and expressed at low levels or not at all in the remaining tissues of the plant. Non-limiting examples of seed-specific promoters include napin, phaseolin, oleosin, and cruciferin promoters. Further examples of suitable regulatory sequences for the proper expression of chitinases, glucanases, osmotin, or PR1, or other genes involved in host defense are known in the art.

Additional regulatory elements may be useful in the nucleic acid constructs of the present invention, including, but not limited to, polyadenylation sequences, translation control sequences (e.g., a ribosome binding site), enhancers, introns, targeting sequences (i.e., a sequence targeting to a particular organefle, such as a plastid), matrix attachment regions (MARs) and the like. MARs are sequence elements that can be added at the ends of cDNA molecules to reduce silencing phenomena. Such additional regulatory elements may not be necessary for expression of the host defense polypeptides, although they may increase expression by affecting transcription, stability of the mRNA or translational efficiency. Such elements can be included in a nucleic acid construct as desired to obtain optimal expression of the host defense nucleic acids in the host cell(s). Sufficient expression, however, may sometimes be obtained without such additional elements.

An example of a nucleic acid construct encoding β-1,3-glucanase, chitinase, PR1, and AP24 that is useful in the invention is provided in FIG. 1. Other suitable nucleic acid constructs may have a 5' to 3' arrangement of the nucleic acids that differs from the construct in FIG. 1, e.g., the arrangement can be chitinase, glucanase, PR1 and osmotin in the 5' to 3' direction. In some embodiments, a first nucleic acid construct may encode one host defense polypeptide and a second construct may encode three host defense polypeptides. In other embodiments, a plurality of nucleic acid constructs are made, each encoding one host defense polypeptide. Each construct can be introduced in the same transformation or can be introduced separated and subsequently combined in a breeding program as described below.

Production of Transgenic Plants

Transgenic plants of the invention can be any crop species, including, for example, Cruciferae plants such as *Brassica* spp. (both low erucic and high erucic acid rapeseed). Suitable *Brassica* species include *B. napus, B. juncea, B. nigra, B. carinata, B. oleracea*, and *B. rapa*. Other suitable species include soybean, sunflower (*Helianthus annuus*), castor bean, peanut, tomato, and flax. Low erucic rapeseed that contains <2% erucic acid and less than 30 μmol of glucosinolates also is known as canola. In some crop species (e.g., rapeseed), plant varieties that have resistance to blackleg and/or sclerotinia can be used. Non-limiting examples of canola varieties that can be used include the registered North American canola varieties Quantum, 46A65, and Q2, which are resistant to the PG2 strain of *P. lingam*, and registered Australian canola varieties Surpass400, Dunkeld, Ranger, Rainbow, and Oscar, which are resistant to the PG3 and PG4 strains of *P. lingam*. In such varieties, resistance to a particular strain or sub-strain of *P. lingam* (e.g., to PG1, PG2, PG3, or PG4) can be improved.

It should be noted that sub-strains of *P. lingam* having different degrees of virulence may be present in different regions of the world, e.g., PG3 strains in Europe and Australia may have different degrees of virulence compared to strains in other geographic regions. In addition, the plant tissue in which fungal disease is most commonly observed may vary between different geographic regions. This can, in turn, reflect sites of fungal attack for which it is desirable to maximize expression of transgenes. Thus, promoters that result in expression of polypeptides in different tissues (e.g., stems vs. leaves) may be especially useful in particular regions.

A plant described herein may be used as a parent to develop a plant line, or may itself be a member of a plant line, i.e., it is one of a group of plants that display little or no genetic variation between individuals for a particular trait. Such lines can be created by several generations of self-pollination and selection for those species amenable to self-pollination. Vegetative propagation from a single parent using tissue or cell culture techniques also can be used. In some embodiments, cytoplasmic male sterility breeding systems can be used to develop lines. Additional breeding techniques to create plant lines are known in the art.

In general, plants of the invention can be obtained by introducing at least one exogenous nucleic acid encoding host defense polypeptides into plant cells. As used herein, the term "exogenous" refers to a nucleic acid that is introduced into the plant. Exogenous nucleic acids include those that naturally occur in the plant and have been introduced to provide one or more additional copies, as well as nucleic acids that do not naturally occur in the plant. Typically, a nucleic acid construct containing a nucleic acid encoding one or more host defense polypeptides is introduced into a plant cell. Seeds produced by a transgenic plant can be bred or otherwise propagated to obtain plants homozygous for the construct. Leaves, seeds, or other tissue can be analyzed to identify those homozygotes having the desired expression of the construct. For example, the polymerase chain reaction (PCR) can be used to determine if seeds or other tissue contains the nucleic acid construct. In some embodiments, a plant expressing one or more host defense polypeptides from a first nucleic acid construct can be crossed or mated with a second plant expressing one or more different host defense polypeptides from a second nucleic acid construct to obtain the desired combination of host defense polypeptides. Seeds produced from the cross can be planted and the resulting plants can be selfed. Leaves, crown stem tissue, seeds, or other tissue can be screened in order to identify those progeny plants expressing the desired combination of host defense polypeptides.

Transgenic plants can be entered into a breeding program, e.g., to increase seed, to introgress the novel construct(s) into other lines or species, or for further selection of other desirable traits. Desirable traits also can be fixed using dihaploid methods for screening and selecting embryos. Additional transgenic plants can be obtained by vegetative propagation of a single transgenic plant, for those species amenable to such techniques.

Progeny of transgenic plants are included within the scope of the invention, provided that such progeny exhibit resistance to *S. sclerotiorum* and/or *P. lingam*. Progeny of an instant plant include, for example, seeds formed on F1, F2, F3, and subsequent generation plants, or seeds formed on BC1, BC2, BC3, and subsequent generation plants.

Transformation techniques for use in the invention include, without limitation, *Agrobacterium*-mediated transformation, polyethylene glycol treatment of protoplasts, electroporation, and particle gun transformation. Illustrative examples of transformation techniques are described in WO 99/43202 and U.S. Pat. No. 5,204,253 (particle gun), U.S. Pat. No. 5,451,513 (plastid transformation) and U.S. Pat. No. 5,188,958 (*Agrobacterium*). Transformation methods utilizing the Ti and Ri plasmids of *Agrobacterium* spp. typically use binary type vectors. Walkerpeach, C. et al., in Plant Molecular Biology Manual, S. Gelvin and R. Schilperoort, eds., Kluwer Dordrecht, C1:1–19 (1994). If cell or tissue cultures are used as the recipient tissue for transformation, plants can be regenerated from transformed cultures by techniques known to those skilled in the art. In addition, various plant species can be transformed using the pollen tube pathway technique.

Plants that have enhanced resistance to *S. sclerotiorum* and/or *P. lingam* (blackleg) can be identified by known techniques, including in vitro tests on plant tissue or field tests. For *S. sclerotiorum*, tests for resistance can be performed by inoculating detached leaves or stems of plants with *S. sclerotiorum* mycelium, then evaluating any resulting necrosis (e.g., measuring length of necrosis) after a period of time sufficient for infection to develop.

Blackleg resistance can be evaluated, for example, by inoculating cotyledons or seedlings with *P. lingam* (the imperfect form of *L. maculans*), and measuring length of necrosis or mean disease severity (MDS) after a period of time sufficient for infection to develop. MDS can be measured on a scale from 0 to 5, with 5 being the worst. Susceptible varieties and highly resistant varieties are used to obtain control values. It is desirable to use a substrain that is prevalent in the geographic region in which the resulting plants are to be utilized for such inoculations and evaluations.

In some embodiments, plants that have enhanced fungal resistance can be identified by in vitro analysis of protein expression levels and subsequent evaluation of in vitro resistance in plant tissue and field resistance of whole plants.

The invention will be further described in the following examples, which do not limit the scope of the invention described in the claims.

EXAMPLES

Example 1

Materials and Methods

The protocol of Radke (1992) *Plant Cell Reports* 11:499) was used to transform *B. napus* variety Westar, which is susceptible to both blackleg and sclerotinia, with plasmid pMOG803. This plasmid contains nucleic acids encoding chitinase, β1,3-glucanase, AP24, and PR1 (all from tobacco). The enhanced 35S promoter from cauliflower mosaic virus was used as the promoter for each of the genes. The plasmid also contains the nptII gene for selection with kanamycin. See, FIG. 1 for a schematic of pMOG803. T0 plants were regenerated from the transformation (150 plants) and selfed to obtain Ti lines (2 to 3 lines/T0 plant). Of the 150 T0 plants, 103 were tested by ELISA for chitinase expression. T2 progeny from 246 T1 lines were representative of each of the 103 T0 plants that were tested by ELISA.

Monitoring of Transformed Plants—Seeds were directly planted in 0.3 L pots, which were then placed in a growing room at 18° C. The plants were repotted 2 weeks later in 5 L pots and placed in greenhouses, where they received 14 hours of light per day, with daylight supplemented with artificial light. Slow-decomposing fertilizer was added upon entry into the greenhouse. Plants were watered a maximum of one time per week and only from underneath, limiting the risks of fungal diseases and problems with aphids. When necessary, treatments against aphids were used without any problem for the pathological tests. No fungicides were used. Self-pollinations were carried out on the adult plants in order to obtain the next generation, with care to minimize risk of fungal contamination and in particular, risk of *Oidium*. Eighteen lines were selected based on expression of chitinase and resistance to *Sclerotinia* on the stem. Each of these 18 lines was derived from a different T0 plant.

Molecular characterization—PCR was performed on 150 T0 plants in order to confirm the presence of pMOG803. Eight T3 plants of each of the 18 selected lines also were tested by PCR. DNA was extracted in a 96-well plate in the following manner. A piece of leaf about 1 $cm^2$ was deposited in each well then freeze-dried over a two day period. Glass beads (two of 4 mm in diameter and two of 2 mm) were added to the freeze-dried leaves, then the leaves were ground using a Polyvotron PV80 for about 20 minutes. After addition of 600 μl of lysis buffer, the plate was incubated at 95° C. for 45 minutes. The lysis buffer was composed, per 100 ml, of: 2.9 g NaCl, 1.2 g Trisma base, and 1.9 mg EDTA. Sodium metabisulfite (72.2 mg) was added immediately before use per 19 ml of lysis buffer. The plate was centrifuged at 10,000 rpm for 15 minutes at 4° C. The supernatant was recovered and the DNA was precipitated by addition of 25 μl of 10 M ammonium acetate and 200 μl of isopropanol. After a few slow inversions, the plate was centrifuged again at 10,000 rpm for 10 minutes at 4° C. Supernatant was removed, 500 μl of 70% ethanol were added to each well, followed by centrifugation at 10,000 rpm for 10 minutes at 4° C. The supernatant then was removed and the plate was dried in a concentrator-evaporator for approximately 15 minutes. The DNA was resuspended in 100 μl of TE, pH 8.8 (1.21 g of Tris and 0.38 g of EDTAper 1 L).

A robot (Biomeck) was used to prepare the PCR reactions in a 96-well plate. The robot deposited 20 μl per well of the reaction mixture and then added 1 μl of DNA solution. The reaction mixture contained, for a final volume of 20 μl, 0.6 μl of primers for amplifying the nptII gene, 0.4 μl of rape plant microsatellite primers, 1.8 μl of dNTPs, 2 μl of 10 X buffer, 0.2 μl of Taq, and sterile water to make up volume to 20 μl. The plate was deposited in a thermocycler in which 30 cycles of PCR were performed using an annealing temperature of 58° C. After PCR, the samples were electrophoresed through an 0.8% agarose gel using TAE as buffer and 10 μl of ethidium bromide per 100 ml of buffer.

Southern—Southern blots were performed on T2 plants (grown in growth chambers) of 50 lines planted in the field. For each line, the analysis was carried out on a mixture of 6 samples derived from different T2 plants. DNA was extracted as described above using about 2 $cm^2$ of plant material, purified by extraction with a mixture of phenol-chloroform-isoamyl alcohol, and precipitated with isopropanol and $(NH_4)_2CO_3$. The DNA was resuspended in 50 μl of TE, pH 8.8 and assayed in a spectrofluorimeter.

For Southern blots, approximately 15 to 20 μg of DNA, which was digested with BamH1, were deposited per well. This enzyme cuts the genome evenly and frequently and within the T-DNA. The restriction digest was carried out at 37° C. overnight using 15–20 μg of genomic DNA, 10 μl of BamH1 at 50 units/μl, 4 μl of 10X buffer, 0.4 μl of 20 mg/ml bovine serum albumin (BSA), and sterile water to 40 μl.

The Southern protocol was performed using a probe corresponding to part of the sequence of the nptII gene and according to the Boehringer Mannheim protocol using digoxigenin and antibodies coupled with phosphatase. Visualization of the bands was carried out by autoradiography, using CDP Star as the reagent for visualization.

ELISA—Two series of ELISA analyses were carried out. The first ELISA analysis was performed on the T2 generation on 6 young plants of each of the 246 T1 lines tested, with 1 well per sample. The second ELISA series was carried out on T3 plants of the 18 lines selected (see FIG. 2). Two analyses were performed on 4 plants per line and 2 wells per sample. An internal series, grouping together transgenic lines with different levels of expression, was used for the ELISAs carried out on the T3 plants.

A small piece of tissue, about 50 $mm^2$, was removed from the tip of a very young leaf and placed in a test tube on ice. For the first series of samples, about 100 μl of extraction buffer were added and the tissue was ground with an electric pestle. In the second series, the tissue was homogenized with metal beads (two of 4 mm in diameter and two of 2 mm)

stirred horizontally by an electrical apparatus. The tubes were centrifuged at 10,000 rpm for 10 minutes at 4° C., the supernatant collected, and its protein concentration measured by the Bradford method.

ELISAs were carried out in a 96-well plate. Approximately 100 µl of a binding solution containing antibodies capable of recognizing the transgenic protein to be measured were deposited in each of the wells. The plate was maintained in a cold room at 4° C. overnight then, the next day, after three rinses of the plate with phosphate buffered saline (PBS), 200 µl of blocking solution were deposited in the wells and incubated for 2 hours at 37° C. After rinsing the plate, 100 µl of a dilute solution of the sample containing 0.1 ng of proteins/µl were deposited in the wells and incubated for 1 hour at 37° C. The plate was rinsed and 100 µl of a solution containing a biotinylated first antibody were deposited in the wells and incubated for 1 hour at 37° C. After rinsing the plate, 100 µl of a solution containing streptavidin peroxidase were deposited in the wells and incubated for 1 hour at 37° C. The plate was rinsed and 100 µl of a solution containing the substrate (ABTS, 2,2'-azino-bis(3-ethylbenzothiazoline-6-sulfonic acid)) were deposited in the wells and incubated for 15 minutes at room temperature. The plate was read in a spectrophotometer at 405 nm.

The composition of the buffers used is (per 1 liter): extraction buffer pH 5.2: 15 ml of 3 M NaAc; binding buffer, pH 9.6: 6.22 g of $NaHCO_3$, 2.75 g of $Na_2CO_3$, and 1 ml of sodium azide; PBS, pH 7.2: 8 g of NaCl, 0.2 g of KCl, and 1.44 g of $Na_2HPO_4$; washing solution: 0.5 ml of Tween 20 in 1 liter of PBS; blocking solution: 7.5 g of BSA in 250 ml of washing solution; substrate solution, pH 4.2: 175 ml of 0.1 M $Na_2HPO_4H_{20}$ to 350 ml of 0.1 M citric acid solution, followed by addition of 250 mg of ABTS to 100 ml of this solution and sterilization with a 0.45 µm filter. Immediately before use, 3 µl of 30% hydrogen peroxide were added to 10 ml of substrate solution.

Western blotting—The preparation of the protein solution and its assay follow the same protocol as that used for the ELISA analyses. For Western blotting, each sample was mixed with 20% (V/V) of 60 mM Tris-base buffer, pH 6.8, containing 5% 2-β-mercaptoethanol, 10% glycerol, 0.01% bromophenol blue, and 1% SDS. Approximately 10 µl of a dilute solution of each sample, equivalent to 4 µg of protein, were boiled for 2 minutes and electrophoresed through a 12.5% acrylamide gel (acrylamide/bisacrylamide: 29/1). Electrophoresis was carried out at a voltage of 80 V at 44 mA for about 2 hours using a migration buffer containing 20 mM Tris-HCl pH 8.8, 150 mM glycine, and 0.1% SDS.

After migration, the gel was electrotransferred for 1 hour onto an Immobilon P membrane (0.45 µm, Milipore) using a buffer containing 20 mM Tris-HCl, pH 8.8, 150 mM glycine, and 20% methanol. The gel and the membrane, which was previously impregnated with pure methanol, were placed between two thicknesses of Whatman paper and compressed between two fibrous nylon pads (e.g., Scotch-Brite® pads). The transfer was carried out at a voltage of 30 V and 122 mA for 1 hour. The membrane then was saturated at 37° C. for 1 hour in buffer A (20 mM Tris-HCl and 500 mM NaCl, pH 7.5) containing 3% food-grade gelatin, and subjected to 4 washes of 5 minutes each in buffer A containing Tween 20 at 0.05%. After incubation overnight at 37° C. in washing buffer containing 1% skim milk and the first antibody directed against the desired protein (rabbit antibody), the membrane was washed 4 times, 5 minutes each, with the same solution (without antibody). The membrane then was incubated with antibody coupled to alkaline phosphate (goat anti-rabbit antibody) in the same buffer for 2 hours at 37° C. After a first wash of 5 minutes in buffer A containing 0.5% of skim milk, three other washes of 5 minutes each were carried out with 100 mM diethanolamine buffer, pH 9.8. The enzymatic reaction was obtained with the mixture of 0.005% BCIP (5-brome-4-chloro-3-indole-phosphate paratoluidine), 0.01% NBT (nitro blue tetrazolium), and 1 mM $MgCl_2$ in the preceding diethanolamine buffer. The reaction was stopped using distilled water baths and the membrane was stored protected from light.

Evaluation of resistance—Four tests were used to evaluate the resistance of the transgenic rape plants: two tests for *sclerotinia* disease resistance (50 lines for *sclerotinia* on stem and 18 lines for *sclerotinia* on leaves) and two tests for blackleg using the line with the best chitinase expression and most resistance to *sclerotinia* disease (line 213). Westar and/or line 205, the null control, were used as the susceptible controls for both blackleg and *sclerotinia* resistance. The spring *B. napus* Dunkeld variety, which is resistant to PG3 and PG4 strains of *P. lingam*, was used as the resistant control for blackleg.

*Sclerotinia*—A test for *sclerotinia* disease in the field was carried out in Europe with consent of the CGB (Commission for Biomolecular Engineering). T2 rape plants were sown at the end of April in a field comprising two blocks, with each block containing 50 randomly distributed lines. In each block, 25 plants of each line were placed in two lines. The inoculation was carried out at the beginning of flowering. A hole was made in the stem of the plant at a height of about 20 cm above the soil surface, and a toothpick on which *S. sclerotiorum* mycelium had developed was introduced into this hole. The percentage of plants infected and the length of necrosis (cm) were measured three weeks later.

Toothpicks containing mycelium were produced as follows. An Erlenmeyer flask containing 45 g of wooden toothpicks (about 500 toothpicks), 5 g of malt, and 500 ml of water was autoclaved and re-autoclaved after 24 hours. Thirty toothpicks were distributed at the periphery of each round Petri dish (14 cm in diameter) containing 120 ml of malt agar and the center of the petri dish was inoculated with mycelium. After culturing the fungus for 4 days at 19° C., approximately ⅔ of each toothpick was covered with fungus and ready to be used for test inoculations.

To test for *sclerotinia* resistance in vitro, fully expanded young leaves having a length of about 10 cm were removed from plants grown in a greenhouse environment and deposited in a square Petri dish (sides 12 cm) containing agar (8 g of technical grade agar per liter, 75 ml per dish). A *S. sclerotiorum* mycelial implant (7 mm in diameter) was deposited at the tip of the leaf and the dishes were kept at 19° C. in an air-conditioned room. The length of necrosis (in cm) was measured five days later. Mycelial implants were prepared by growing the fungus on agar-containing water for four days then subculturing onto potato dextrose agar (PDA) medium for two days. The test was carried out on the T3 generation of the 18 lines selected. Four plants from each of the 18 lines were evaluated, using three leaves from each plant. Two successive sowings were necessary to carry out the test.

Blackleg—The Williams test (*phoma* test on cotyledons) was performed on the Dunkeld variety, the 213 line, and on a null control to evaluate blackleg resistance. See Williams and Delwiche, 1979 Cruciferae conference, page 164. Eight flats, each containing 10 rape plants of each line, were used for this test. The rape plants were sown in a flat containing a greenhouse soil mixture and maintained at 25° C. until the test was ready to be performed. The plants were watered and fertilized. Two weeks after sowing, the rape plants were staked. Young leaves were systematically removed up to the day of the inoculation, which was one month after sowing. A small hole was made in each cotyledon lobe before inoculation and 10 µl of a suspension of pycnidiospores (500,000 spores/ml) were deposited in each hole. The flats were placed in cloches for two days. Necrosis length was measured two weeks later.

Pycnidiospores were obtained from the *Phoma* PG3 strain by growing on V8 medium under near ultraviolet light and recovering the pycnidiospores in sterile water (pink droplets). The mixture was filtered in order to remove impurities.

A *phoma* test on the stem was carried out on the Dunkeld variety, line 213, line 205 (null control), and on progeny of Dunkeld x 213 and Dunkeld x control crosses. About 30 plants of each line were randomly placed in a greenhouse and were inoculated at the three-leaf stage. A 3 mm hole was made in the stem at about 5 cm from the soil and 10 µl of a suspension of pycnidiospores (a suspension of 500,000 pycnidiospores/ml pregerminated for 4 days with 10 mM glucose) were placed in the hole. The site of inoculation was covered in order to maintain moisture. Fogging was carried out immediately after the inoculation and on the following two days to increase humidity. Necrosis length was measured approximately 45 days later.

Statistical analyses—All statistical analyses were performed by ANOVA with the STATITCF software. The statistical test used was the Newman-Keuls test. Differences between sample means were considered significant at a level of $p<0.05$.

Example 2

Selection of Lines and Pathological Evaluations

Figure 2:
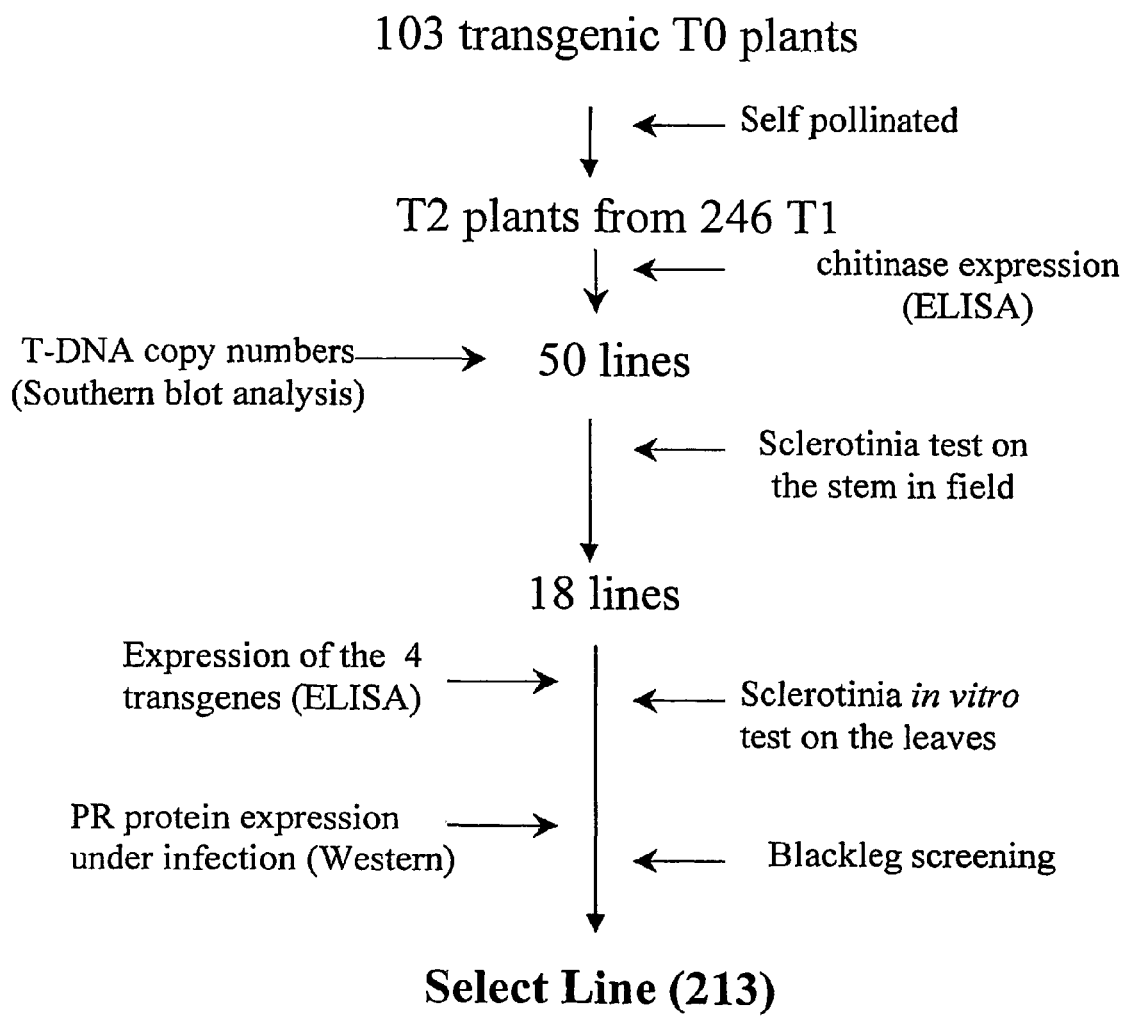

Expression of the tobacco chitinase was examined in leaves of the T2 progeny of 246 T1 lines (FIG. 2). Expression was determined by ELISA and was performed on 6 plants per line. Chitinase expression was variable, ranging from 0 to 0.18% of the protein relative to the total quantity of soluble proteins. A null control, line 205 (Westar which had been subjected to a mock transformation), showed no chitinase expression by ELISA, even during infection with *S. sclerotiorum*. The absence of expression in this control during infection suggested that the tobacco antibodies may have low recognition of endogenous rape plant chitinases.

Fifty independent lines were selected for further evaluation of the resistance to *S. sclerotiorum*. These 50 lines had a broad range of chitinase expression levels.

To analyze the progeny of each line, the number of copies and the number of insertion sites in the event of lines with several copies were determined. This information was used to understand the type of segregation to be expected for each line. For example, in lines with one insertion, a segregation with ¾ of transformed plants and ¼ of nontransformed plants was expected. Selection with kanamycin, or screening by ELISA or PCR was used to eliminate the latter.

Southern blots were carried out with a probe corresponding to a portion of the nptII gene. Results revealed a majority of T1 lines with a single copy (76%), a percentage greater than that observed on the T0 plants (Table 1).

TABLE 1

|  | T0 PLANTS | T1 LINES |
| --- | --- | --- |
| 1 copy | 42% | 76% |
| 2 copies | 36% | 16% |
| >2 copies | 21% | 8% |

In the second step of selection, a *S. sclerotiorum* disease test on the stem was used to identify lines resistant to *S. sclerotiorum*. This test was carried out on two repeats of 20 plants for each of the 50 lines. Two measurements of infection were performed: the percentage of infected plants and the length of necrosis thereof.

The percentage of infected plants was variable between the transgenic lines, with the percentage of infection ranging from 0 to 100%. For the best lines, this percentage was about 20% versus 65% for the null control. Thus, resistance on the stem was improved in the transgenic plants. Necrosis length ranged from 0 to 40 cm and was correlated with the percentage of infected plants ($R^2=0.8$). For the best lines, the fungus was slowed by about 20% relative to the null control.

Of the 50 tested lines, 18 lines were chosen based on resistance to *sclerotinia* (~0 to 40% of leaves infected), level of chitinase expression on the leaf (~65 to 113 relative to line 213), or both. A few of the 18 lines did not exhibit high levels of chitinase expression or increased resistance to *S. sclerotiorum*. Further studies were performed on T3 plants.

*Sclerotinia* disease tests on detached leaves were carried out to evaluate the resistance on the leaf, one of the first organs affected by the fungus. Three plants from each of the 18 selected lines (T3 generation) were evaluated by this test using a single leaf from each plant. This test was replicated three times. Two successive sowings were necessary in order to carry out this test. The test was scored by measuring, on the fifth day after inoculation, the necrosis length along the midrib of the leaf, which was from the mycelial implant up to the boundary for migration of the fungus. The results showed a variation in the necrosis length ranging from 4 to 6 cm, and demonstrated a significant difference between the best lines and line 205 (null control). Line 213 had a necrosis length of 4.2±0.7 cm vs. 6.0±0.4 for line 205. For these lines, the rate of propagation of the fungus was decreased by about 30%, a resistance equivalent to the resistant Dunkeld variety, for which the average necrosis length was 4.2 cm. Nine out of 12 lines resistant for *sclerotinia* disease on the stem also were resistant on the leaf. The correlation was $R^2=0.5$. Line 138, which showed resistance on the stem but not on the leaf, was excluded from the correlation.

In summary, a genetic construct with the four host defense proteins provided significant resistance to *S. sclerotiorum* on the leaf and stem in the selected lines.

Example 3

*Phoma* Tests For Blackleg Resistance

A qualitative *phoma* test on the cotyledons was carried out on line 213, which had one of the best chitinase expression levels and one of the best resistances to *sclerotinia*, using the PG3 *Phoma* strain. The experiment was carried out on 4 cotyledon lobes X 10 plants X 8 flats. Line 213 had statistically significant resistance to blackleg compared to the null control (line 205), with 13 mm of necrosed tissue for line 213 versus 11.8 mm for line 205. The fungus was slowed by about 9% compared with line 205.

A *phoma* test on the stem also was carried out on line 213 (30 plants for line 213 and control). Necrosis length (measured 6 weeks after inoculation) was 10.2±2.6 cm for line 213, 10.3±3.6 cm for line 205, and 3.4±1.0 cm for the resistant variety Dunkeld. No significant differences in resistance toward *phoma* on the stem were observed between line 213 and line 205. Since the selection was carried out initially for chitinase expression and resistance to *sclerotinia* on the stem, it is possible that lines having higher resistance than line 213 to *phoma* on stems were not selected.

See Examples 9 and 10 for results when lines were selected directly for resistance to the PG2 strain of *Phoma*.

Example 4

Expression of Transgenic Proteins in Rape Plants

Expression studies were carried out on the T3 generation of the 18 lines selected above. Expression of the four transgenes was examined by ELISA in leaf or stem tissue using two independent tests of four plants per line, with two replicates per plant. Table 3 provides the expression levels of the transgenes. All expression values are relative to line 213, whose value is 100.

Chitinase—There was a broad range of chitinase expression levels in leaves in the T3 generation among the different lines. In addition, in some lines, the expression level in the T3 generation was different from that observed in the T2 generation. Chitinase expression in the T3 generation accounted for a maximum of 0.05% of total soluble protein, whereas it was up to 0.18% in the T2 generation.

In order to evaluate the differences in expression between the generations, an ELISA with the 213 and 187 lines was carried out. Samples of the T2, T3, and T4 generations of each line were placed on the same plate in order to remove any possible bias. Six plants were analyzed for each case with two wells per sample. The results (Table 2) indicated that the expression level of chitinase was reduced after the T2 generation, although the T3 and T4 generations each had the same level of expression.

Expression of chitinase in the stem was very similar to that obtained on the leaf (a maximum of about 0.06% of soluble protein).

TABLE 2

|  | Chitinase expression relative to chitinase expression in the $T_3$ generation of line 213 |
| --- | --- |
| Line 213, $T_2$ | 170 |
| Line 213, $T_3$ and $T_4$ | 100 |
| Line 187, $T_2$ | 178 |
| Line 187, $T_3$ and $T_4$ | 84 |
| Non-transformed control 205 | 0 |

Glucanase—Leaf glucanase expression levels were similar to chitinase expression levels in the T3 generation. The percentage of glucanase relative to the quantity of total soluble protein was almost identical to that of chitinase, with glucanase accounting for a maximum of about 0.04% of total soluble protein. Expression levels of glucanase in the stem were similar to that obtained on the leaf, with tobacco glucanase accounting for a maximum of about 0.05% of soluble proteins.

PR1 and AP24—PR1 expression also showed a broad range of expression levels among lines, but the levels of expression were lower than for glucanase or chitinase. PR1 accounted for a maximum of 0.02% of the total soluble protein. A broad range of expression levels also were observed with AP24, although the absolute levels of expression were higher than that for the other three transgenes. AP24 accounted for up to 0.13% of the total soluble protein, close to the value of chitinase in the T2 generation.

TABLE 3

| | Expression in Uninfected Leaves* | | | | Expression in Leaves Infected With *S. Sclerotiorum** | | Expression in Uninfected Stems* | | Sclerotinia Test on Stem (% of infected leaves)** | Sclerotinia Test on Leaves (necrosis length centered and reduced[a])*** |
| --- | --- | --- | --- | --- | --- | --- | --- | --- | --- | --- |
| | Gluc | Chit | AP24 | PR1 | Gluc | Chit | Gluc | Chit | | |
| 55 | 9 | 28 | 154 | 7 | 27 | 25 | 8 | 21 | 58 | 0.8 |
| 65 | 62 | 113 | 103 | 31 | 120 | 122 | 7 | 61 | 59 | −0.3 |
| 68 | 12 | 28 | 2 | 22 | 8 | 10 | 6 | 0 | 88 | 0.6 |
| 87 | 0 | 49 | 32 | 0 | 67 | 101 | 97 | 162 | 54 | 0.7 |
| 91 | 0 | 0 | 0 | 0 | 14 | 0 | 8 | 8 | 100 | 0.6 |
| 94 | 78 | 94 | 76 | 116 | 44 | 65 | 62 | 66 | 42 | −0.4 |
| 98 | 6 | 0 | 127 | 0 | 4 | 0 | 4 | 2 | 34 | 0.2 |
| 117 | 5 | 0 | 150 | 0 | 3 | 0 | 4 | 0 | 18 | 0 |
| 132 | 57 | 31 | 33 | 122 | 60 | 63 | 88 | 86 | 66 | 0 |
| 138 | 5 | 23 | 110 | 105 | 26 | 56 | 17 | 37 | 17 | 0.7 |
| 150 | 120 | 82 | 108 | 113 | 142 | 79 | 70 | 104 | 40 | −0.4 |
| 158 | 0 | 72 | 127 | 121 | 3 | 62 | 3 | 147 | 0 | −0.1 |
| 187 | 89 | 79 | 59 | 81 | 95 | 65 | 92 | 76 | 8 | −0.4 |
| 205 | 0 | 0 | 2 | 0 | 2 | 0 | 1 | 0 | 63 | 0.7 |
| 213 | 100 | 100 | 119 | 58 | 100 | 100 | 99 | 100 | 25 | −0.7 |
| 218 | 44 | 76 | 68 | 67 | 78 | 64 | 51 | 68 | 57 | −0.2 |

TABLE 3-continued

| | Expression in Uninfected Leaves* | | | | Expression in Leaves Infected With *S. Sclerotiorum** | | Expression in Uninfected Stems* | | Sclerotinia Test on Stem (% of infected leaves)** | Sclerotinia Test on Leaves (necrosis length centered and reduced[a])*** |
|---|---|---|---|---|---|---|---|---|---|---|
| | Gluc | Chit | AP24 | PR1 | Gluc | Chit | Gluc | Chit | | |
| 220 | 70 | 65 | 59 | 104 | 102 | 44 | 120 | 29 | 45 | −0.3 |
| 224 | 34 | 54 | 116 | 79 | 88 | 77 | 47 | 71 | 58 | 0.2 |

Figure 3:
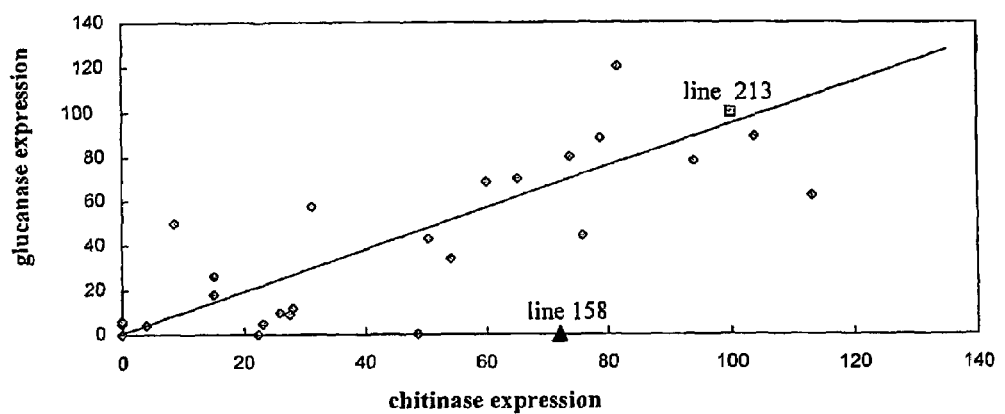

*S.E.M. for expression levels was ±20;
**S.E.M. was ±12;
***S.E.M. was ±0.3,
[a]refers to the ((value of the individual) − (mean of the group))/standard deviation of group There appeared to be a correlation between glucanase and chitinase expression in leaves among the 18 tested lines (FIG. 3), indicating that the transgenes from the same transformation event were regulated similarly. $R^2=0.6$ for all 18 lines; $R^2=0.7$ when lines 158 and 87 were excluded. Given the apparent correlation between glucanase and chitinase expression, the expression values for these two proteins were grouped together in the form of a glucanase-chitinase average relative to the 213 line to increase the accuracy of the intrinsic value of each line for glucanase and chitinase expression. The 158 and 87 lines had high glucanase expression without any chitinase expression (for line 158, chi=72 and glu=0, for the 87 line, chi=49 and glu=0).

An apparent correlation also was observed between glucanase and chitinase expression in the stem. When lines 98, 117, 158 and 220 were excluded, $R^2=0.9$, indicating that regulation of the glucanase and chitinase transgenes in the stem was similar to that of the leaves.

The results indicate that *sclerotinia* resistance on the stem and leaf can be obtained with expression of various combinations of transgenes.

Example 5

Chitinase and Glucanase Expression in Leaves Infected with *Sclerotinia*

Expression levels of chitinase and glucanase were measured in infected leaves to determine if transgenes were differently regulated during infection and to determine if endogenous chitinases and glucanases were expressed during infection. The study was carried out by ELISA using detached leaves that were subjected to the *sclerotinia* disease test in vitro. Two plants from each line were evaluated, using four separate ELISA reactions and two wells per sample.

Glucanase and chitinase levels during infection were identical to those observed in uninfected leaves. Tested lines also exhibited the same expression relative to each other. The correlation observed between glucanase-chitinase expression on the uninfected leaf and glucanase-chitinase expression on the infected leaf was $R^2=0.8$ (Table 3).

Example 6

Comparison of the Expression of the Hemizygotes Relative to the Homozygotes

In order to compare hemizygotes to their respective homozygotes, three crosses were carried out: 213xWester, 218xWester, and 187xWester. Chitinase expression was measured by ELISA using three F1 plants from each cross per analysis for the 218xWester and 187xWester crosses and 8 F1 plants from the 213XWestar cross for each analysis. Each sample was analyzed in two different wells. Analysis of the F1 progeny indicated that the chitinase transgene acted in a dominant fashion.

In order to study the influence of genetic background on the expression of the transgenes, line 213 was crossed with the resistant Dunkeld variety or with Westar (sensitive variety) and expression profiles were compared in F1 progeny through ELISA analyses. The experiment was carried out with eight plants per analysis and two wells per sample. The results are presented as a relative value with respect to line 213 (Table 4).

TABLE 4

| | Chitinase Expression in Leaves Relative to Line 213 | Glucanase Expression in Leaves Relative to Line 213 |
|---|---|---|
| 213 | 100 | 100 |
| Progeny of 213 × Dunkeld | 152 | 502 |
| Progeny of 213 × Westar | 94 | 164 |
| Westar × Dunkeld | 0 | 0 |
| Westar | 0 | 0 |

Expression of chitinase in progeny of the 213x Dunkeld crossing was significantly greater than for progeny of the 213xWester crossing (chi=152 vs. 94). Progeny of the 213x Dunkeld crossing also expressed significantly more glucanase than progeny of the 213xWester crossing (glu=502 vs.164). These results suggest that genotype may modify the expression level of these transgenes.

To evaluate expression in transgenic progeny, three crosses were carried out: 213×218, 213×187, and 218×187. F1 progeny were hemizygous for each transformation event. Chitinase expression was analyzed by ELISA with 6 plants per analysis. The results (Table 5) show that the level of expression of the F1 progeny does not correspond to the sum of the levels of expression of each parent. The results thus indicate such progeny maintain expression at a level close to that of a single transformation event with some influence of parental expression. There is a significant difference between progeny of 213×187 and 218×187 at a level of $p<0.01$ by the Newman Keuls test.

TABLE 5

| | Chitinase Expression on Leaves Relative to 213 Line |
|---|---|
| 213 | 100 |
| 187 | 88 |
| 218 | 60 |
| F1 progeny of 213 × 218 | 107 |
| F1 progeny of 213 × 187 | 133 |
| F1 progeny of 218 × 187 | 93 |
| 205 | 0 |

Example 7

Chitinase Expression in Cotyledons

As described above, the 213 line was tested for resistance to the PG3 strain of *phoma* on the cotyledons and was found to have some resistance. Accordingly, the level of expression of chitinase was measured in this organ of the plant. Chitinase expression was analyzed by ELISA on six plants per analysis and two wells per sample. The tobacco chitinase reached a value of 191 in cotyledons versus 100 in leaves for the 213 line.

Example 8

Influence of the Expression of the Transgenes on the Natural Resistance of Rape Plant to the *Sclerotinia* Disease and to *Phoma*

Western blots were performed on the 213, 187 and 224 lines, on the null control (line 205), and on the resistant Dunkeld variety, during three independent *sclerotinia* disease tests on the leaf. The study was carried out on a band of tissue (3 mm in width) from the front of the infection as it advanced from the tip of the leaf to the petiole. Samples of leaves subjected to the test conditions, and therefore stressed, but not infected with *S. sclerotiorum*, also were collected. Samples of leaves collected from the whole plant also were used as a control.

In examining expression of glucanase in the absence of stress, only transgenic glucanase was observed. Under stress conditions, but with no infection, a new band having a higher molecular weight appeared in both the transformed lines and null control. In most cases, this band was more dense for the transformed lines.

After infection with *S. sclerotiorum*, a new band appeared that was intermediate in migration compared with the first two. At the $2^{nd}$ day after infection (D+2), this band was of the same intensity for the transformed lines and null control, while at the $5^{th}$ day after infection (D+5), this band had a variable intensity in the transgenic lines. Line 213 showed a less intense band and line 187 had a more intense band when each were compared with the null control.

In the null control at the D+2 stage of infection, the rape plant band observed during stress had reached the same intensity as that of the transformed lines. However, this band remained weaker at the D+5 stage.

With respect to chitinase expression, only a band having the apparent molecular weight of the transgenic chitinase appeared in nonstressed healthy tissues. Under stress conditions, but in the absence of infection, no bands were observed in the null line. In three independent tests performed on detached leaves. Two different profiles were observed in two of the tests, two new bands appeared, whereas in the third test, three bands were visible, including the two bands from the other independent test, with the same intensity for the three tests.

As these new proteins were present only in the transgenic lines, they were linked to the presence of the transgenes. The new proteins could be endogenous chitinases or degradation products of the tobacco chitinase.

Under the conditions for infection with *S. sclerotiorum*, all the lines, as well as the null control, have two new bands having molecular weights greater than the chitinases previously described in the stressed tissues. They are of the same intensity for all the lines. This chitinase, present solely in the transgenic lines, was therefore linked to the presence of the transgenes. Again, the new bands observed on the Western blot could represent endogenous chitinases or degradation products.

To study the influence of the expression of the transgenes on the specific resistance of the Dunkeld variety to phoma, two crossings were carried out: Dunkeld×213 and Dunkeld x line 205 (null control), as described above. ELISA results confirmed the expression of the tobacco chitinase and glucanase in the Dunkeld x 213 F1 progeny. The evaluation of the resistance to *phoma* was carried out using the test on the stem with the PG3 strain. A preliminary test on the cotyledons showed that the Dunkeld variety possesses the resistance gene(s) corresponding to this strain.

The results (Table 6) show that line 205 and line 213 have the same stem sensitivity to the PG3 *phoma*. It also may be noted that the Dunkeld x line 205 hybrid has a new intermediate resistance between the Dunkeld resistance and the line 205 sensitivity, the differences being significant. No difference was observed between F1 progeny derived from Dunkeld x 213 crossings and F1 progeny derived from the Dunkeld x 205 crossing.

TABLE 6

| Lines | Length of Necrosis (cm) |
|---|---|
| Dunkeld | 3.4 ± 1.0 |
| F1 progeny of Dunkeld × 205 | 6.2 ± 1.6 |
| F1 progeny of Dunkeld × 213 | 6.3 ± 1.8 |
| F1 progeny of 205 × 213 | 9.7 ± 3.5 |
| Line 213 | 10.2 ± 2.6 |
| Line 205 (control) | 10.3 ± 3.6 |

Example 9

Selection for Blackleg Resistance

*B. napus* variety Westar transgenic lines were prepared as described in Example 1. PCR was used to select T1 lines that contained complete insertions using primers for glucanase, PR1, and nptII. The T1 lines were propagated to the T3 generation, at which time field and laboratory evaluations were started. In field tests, growth and development of the T3 to T5 transgenic lines appeared normal to controls. No abnormal morphologic traits were observed and seed size was similar to the checks.

Transgenic lines were evaluated for improved resistance to blackleg or *sclerotinia*. Typically, four independent experiments were performed with four plants in each experiment, for a total of 16 seedlings. Westar, resistant line NS2186, and moderate resistant line NS2173 were used as checks in the test. For blackleg resistance, an inoculation test was performed at the cotyledon stage in growth chambers using the PG2 *Phoma* strain. MDS was measured on two cotyledons on a scale from 0–5, with 5 being the worst. Ten T4 lines, which were PCR positive at the T3 stage, were tested. The results are showed in Table 7. Westar had an MDS score of 4.95, while resistant varieties Quantum and NS2186 had average scores of 1.53 and 1.45, respectively. The moderately resistant variety NS2173 had an MDS score of 1.98. Moderately susceptible varieties Legend and Excel had MDS scores of 2.98 and 3.15, respectively. The disease severity ranged of T4 lines from 2.8 to 5.0.

Three T4 lines (97FM01132-01, 97FM01532-01 and 97FM00932-01) showed significant improvement over Westar with scores of 2.83, 2.83, and 3.38, respectively (LSD$_{0.05}$ is 0.66).

TABLE 7

Inoculation Test of T4 Lines at Cotyledon Stage for Blackleg Resistance

| Line ID | No. reps | Mean severity | % WS[1] | CV[2] | Westar severity in tray |
|---|---|---|---|---|---|
| 97FM01132-01 | 4 | 2.83 | 60.2 | 25.6 | 4.7 |
| 97FM01532-01 | 4 | 2.83 | 59.6 | 19.0 | 4.7 |
| NS2173 | 4 | 1.98 | 44.2 | 23.9 | 4.5 |
| 97FM00932-01 | 4 | 3.38 | 72.3 | 21.8 | 4.7 |
| NS2186 | 4 | 1.45 | 28.8 | 36.3 | 5.0 |
| Excel | 4 | 3.15 | 63.0 | 18.2 | 5.0 |
| Legend | 4 | 2.98 | 63.0 | 11.8 | 4.9 |
| Quantum | 4 | 1.50 | 30.4 | 29.3 | 4.8 |
| Westar | 4 | 4.95 | 99.0 | 2.0 | 5.0 |
| Mean | | 2.78 | | | |
| CV | | 19.52 | | | |
| LSD 0.05 | | 0.66 | | | |

[1]Disease severity relative to Westar control.
[2]Coefficient of variation.

Field evaluations of blackleg resistance also were performed on T4 plants. The MDS were calculated based on 25 plants scored at maturity. Conditions were not ideal for disease development, even with artificial inoculation at seedling stage (average disease incidence of 82%). Westar, resistant line NS2186, and moderate resistant line NS2173 were used as checks in the test. Again, disease severity was measured on a scale from 0 to 5, with 5 being the worst. In the field evaluation (Table 8), Westar had an MDS score of 2.6 and a mean disease incidence of 79%. Resistant line NS2186 had an MDS score of 1.5 with a disease incidence of 76% and moderately resistant line NS2173 had an MDS score of 1.8 with a disease incidence of 76%. Four T4 lines showed blackleg resistance improvement over Westar: Line 97FM01617-01 had a score of 1.7 with disease incidence of 80%; line 97FM01625-01 had a score of 1.4 with disease incidence of 76%; line 97FM01723-01 had a score of 1.7 with disease incidence of 68%; and line 97FM0172801 had a score of 1.4 with disease incidence of 72%. No statistical analysis was carried as only one replication was tested and due to low disease incidence in the field.

TABLE 8

Field Test Results for Blackleg Resistance of T4 Lines

| Line ID | MSD | Disease Incidence |
|---|---|---|
| 97FM01617-01 | 1.7 | 80.0 |
| 97FM01625-01 | 1.4 | 76.0 |
| 97FM01723-01 | 1.7 | 68.0 |
| 97FM01728-01 | 1.4 | 72.0 |
| WESTAR | 2.8 | 84.0 |
| WESTAR | 2.6 | 80.0 |
| WESTAR | 2.3 | 72.0 |
| NS2173 | 1.8 | 76.0 |

Lines that showed improvement over Westar in the cotyledon test or in the field test were tested again. In both tests, varieties Westar, Quantum, and Legend were used as checks. As indicated in Table 9, the inoculation test of cotyledons was carried out on two randomized blocks due to a large number of candidates. In Block A, Westar had a score of 4.08; Quantum had a score of 2.75; and Legend had a score of 3.63. Again, line 97FM01625-03, line 97FM01625-08, line 97FM01913-02, and line 97FM01728-07 showed significant improvement over Westar with scores of 2.88, 3.00, 2.13, and 3.08, respectively, versus 4.08 for Westar. In Block B, Westar had an MDS of 4.30; Quantum had an MDS of 2.33; and Legend had an MDS of 3.78. Lines 97FM00932-09 and 97FM01625-03 showed significant improvements over Westar with an MDS of 1.5 and 3.08, respectively, versus a MDS of 4.30 for Westar.

TABLE 9

Inoculation Test at Cotyledon Stage in T5 Plants for Blackleg Resistance

| ARC LINE | Line ID | No. reps | Mean severity (0–5) | Percent of Westar | CV | Percent of Westar rank |
|---|---|---|---|---|---|---|
| | | | Block A | | | |
| 99A45 | 97FM00932-09 | 4 | 3.58 | 88.0 | 24.0 | 24 |
| 99A27 | 97FM01625-03 | 4 | 2.88 | 79.2 | 25.5 | 12 |
| 99A32 | 97FM01625-08 | 4 | 3.00 | 76.3 | 30.3 | 11 |
| 99A47 | 97FM01913-02 | 4 | 2.13 | 53.8 | 29.4 | 7 |
| 99A24 | 97FM01617-07 | 4 | 3.10 | 76.0 | 15.4 | 18 |
| 99A13 | 97FM01726-01 | 4 | 3.10 | 76.0 | 15.4 | 17 |
| 99A37 | 97FM01728-07 | 4 | 3.08 | 75.5 | 14.1 | 15 |
| 99AW1 | ARC Westar | 4 | 4.08 | 100.0 | 27.9 | 36 |
| 99ALeg | Legend | 4 | 3.63 | 92.3 | 8.5 | 26 |
| 99A58 | Quantum | 4 | 2.75 | 67.4 | 16.5 | 10 |

TABLE 9-continued

Inoculation Test at Cotyledon Stage in T5 Plants for Blackleg Resistance

| ARC LINE | Line ID | No. reps | Mean severity (0–5) | Percent of Westar | CV | Percent of Westar rank |
|---|---|---|---|---|---|---|
| Mean | 3.09 | | | | | |
| CV | 22.73 | | | | | |
| LSD 0.05 | 0.85 | | | | | |
| | | Block B | | | | |
| 99BA45 | 97FM00932-09 | 4 | 1.50 | 41.7 | 39.6 | 1 |
| 99BA27 | 97FM01625-03 | 4 | 3.08 | 78.0 | 33.9 | 8 |
| 99BW1 | ARC Westar | 4 | 4.30 | 95.8 | 16.4 | 32 |
| 99BLeg | Legend | 4 | 3.78 | 100.2 | 15.5 | 24 |
| 99BQuant | Quantum | 4 | 2.33 | 65.6 | 30.1 | 6 |
| Mean | 2.90 | | | | | |
| CV | 27.02 | | | | | |
| LSD 0.05 | 0.99 | | | | | |

In the field tests on T5 plants, Westar and Quantum were used as checks. For each test entry, 50 plants were evaluated from a minimum of two replicates of naturally infected plants. Tests results are presented in Table 10. Each line ID number in Table 10 represents two replicated sets of data. The following lines showed improved disease resistance over Westar: Line 97FM01913-02 had an MDS of 3.36; line 97FM00932-09 had an MDS of 3.4, with one plot having a score of 2.94; line 97FM01617-01 had a score of 3.82; line 97FM01625-01 had a score of 3.83; line 97FM01625-03 had a score of 3.55; line 97FM01625-08 had a score of 3.32; and line 97FM01728-01 had a score of 3.63.

TABLE 10

Field Test Results for Blackleg Resistance in T5 Plants

| Line ID | MDS | CV | Rank |
|---|---|---|---|
| 97FM01913-02 | 3.36 | 45.3 | 5 |
| 97FM00932-09 | 2.94 | 31.7 | 2 |
| 97FM00932-09 | 3.66 | 31.9 | 10 |
| 97FM00932-09 | 3.52 | 28.9 | 9 |
| 97FM00932-09 | 3.48 | 45.5 | 7 |
| 97FM01617-01 | 3.82 | 15.5 | 14 |
| 97FM01625-01 | 3.82 | 25.9 | 15 |
| 97FM01625-01 | 3.84 | 11.8 | 18 |
| 97FM01625-03 | 3.70 | 17 | 12 |
| 97FM01625-03 | 3.87 | 2 | 19 |
| 97FM01625-03 | 3.08 | 40.2 | 3 |
| 97FM01625-08 | 3.46 | 10.6 | 6 |
| 97FM01625-08 | 3.18 | 34.5 | 4 |
| 97FM01728-01 | 3.51 | 23.8 | 8 |
| 97FM01728-01 | 3.74 | 36.7 | 13 |
| Quantum | 2.22 | | 1 |
| Westar | 4.65 | | 100 |
| Mean | 3.52 | | |
| CV | 28.21 | | |
| LSD 0.05 | 1.73 | | |

Example 10

Field Selection For *Sclerotinia* Resistance

Field tests for *sclerotinia* resistance were performed as described above on T4 lines (and one T3 line) that were positive by PCR. Test results are provided in Table 11. In this table, "5d", "10d" and "15d" refer to the number of days after infection and the numbers in these columns refer to the lesion size in cm. "Inct" refers to the number of plants used to score for disease. Susceptible variety Westar and resistant variety C022 were used as checks in the test. Westar (CK2) had a lesion size of 4.4 cm 5 days after infection, a lesion size of 12.0 cm 10 days after infection, and a lesion size of 18.1 cm 15 days after infection. Resistant check 022 (CK4) had a lesion size of 3.1 cm 5 days after infection; a lesion size of 7.2 cm 10 days after infection, and a lesion size of 11.4 cm 15 days after infection. In a separate test, C022 had a lesion size of 2.1 cm 5 days after infection, a lesion size of 5.7 cm 10 days after infection, and a lesion size of 12.4 cm 15 days after infection.

Seven lines showed substantial improvement over Westar. Line 97FM01625-02 had lesion size of 2.3 cm 5 days after infection, 6.3 cm 10 days after infection, and 10.9 cm 15 days after infection. Line 97FM01625-03 had a lesion size of 2.5 cm 5 days after infection, 7.5 cm 10 days after infection, and 12.9 cm 15 days after infection. T3 line 97FM01421-01 had a lesion size of 2.3 cm 5 days after infection, 5.9 cm 10 days after infection, and 12.8 cm 15 days after infection.

TABLE 11

Field test for Sclerotinia Resistance in T3 and T4 Plants

| Treatment | 5 d | inct. | 10 d | inct. | 15 d | inct. |
|---|---|---|---|---|---|---|
| 97FMO0932-01 | 4.3 | 18 | 11.0 | 19 | 16.6 | 14 |
| 97FMO1233-03 | 4.2 | 20 | 10.2 | 20 | 15.3 | 15 |
| 97FMO1330-01 | 4.1 | 22 | 11.0 | 22 | 16.6 | 22 |
| 97FMO1331-04 | 4.0 | 21 | 11.7 | 21 | 19.0 | 22 |
| 97FMO1419-01 | 5.0 | 24 | 12.3 | 24 | 19.7 | 23 |
| 97FMO1421-01* | 4.7 | 22 | 10.7 | 23 | 18.4 | 23 |
| 97FMO1421-01.T3 | 2.3 | 14 | 5.9 | 15 | 12.8 | 15 |
| 97FMO1526-04 | 4.4 | 22 | 11.2 | 21 | 17.6 | 21 |
| 97FMO1527-02 | 5.2 | 23 | 11.6 | 23 | 18.7 | 22 |
| 97FMO1532-01 | 4.5 | 20 | 10.9 | 19 | 15.9 | 17 |
| 97FMO1615-01 | 4.1 | 22 | 11.2 | 22 | 18.0 | 20 |
| 97FMO1617-01 | 3.5 | 19 | 9.5 | 20 | 15.6 | 17 |
| 97FMO1617-03 | 3.6 | 20 | 9.9 | 22 | 16.5 | 21 |
| 97FMO1617-04 | 3.8 | 18 | 9.1 | 18 | 16.0 | 19 |
| 97FMO1617-05* | 3.5 | 19 | 8.1 | 19 | 14.7 | 19 |
| 97FMO1617-06 | 4.1 | 19 | 9.5 | 20 | 16.8 | 19 |
| 97FMO1617-08 | 4.6 | 18 | 11.0 | 19 | 17.7 | 19 |
| 97FMO1625-01 | 5.7 | 19 | 11.3 | 19 | 17.9 | 19 |
| Quantum (CK1) | 3.1 | 21 | 9.6 | 24 | 16.1 | 24 |
| Westar (CK2) | 4.4 | 21 | 12.0 | 21 | 18.1 | 21 |

TABLE 11-continued

Field test for Sclerotinia Resistance in T3 and T4 Plants

| Treatment | 5 d | inct. | 10 d | inct. | 15 d | inct. |
|---|---|---|---|---|---|---|
| 97FMO1625-02 | 2.3 | 15 | 6.3 | 14 | 10.9 | 11 |
| 97FMO1625-03 | 2.5 | 13 | 7.5 | 14 | 12.9 | 14 |
| 97FMO1625-04 | 2.1 | 12 | 7.6 | 15 | 15.6 | 12 |
| 97FMO1625-05 | 1.7 | 10 | 7.7 | 15 | 14.7 | 15 |
| 97FMO1625-06 | 2.7 | 15 | 6.4 | 15 | 16.2 | 14 |
| 97FMO1625-07 | 3.4 | 17 | 9.7 | 20 | 14.1 | 13 |
| 97FMO1625-08 | 2.5 | 15 | 7.6 | 15 | 15.0 | 14 |
| 97FMO1723-01 | 4.5 | 19 | 10.9 | 18 | 16.4 | 13 |
| 97FMO1724-03 | 4.7 | 18 | 12.6 | 19 | 18.5 | 18 |
| 97FMO1726-01 | 5.3 | 18 | 11.4 | 20 | 17.1 | 20 |
| 97FMO1728-01 | 2.2 | 11 | 7.1 | 14 | 15.3 | 16 |
| 97FMO1728-03 | 3.8 | 18 | 7.8 | 18 | 15.4 | 16 |
| 97FMO1728-04 | 2.4 | 15 | 5.4 | 14 | 13.8 | 15 |
| 97FMO1728-05* | 3.8 | 20 | 10.3 | 20 | 16.4 | 19 |
| 97FMO1728-06* | 3.6 | 17 | 9.9 | 20 | 15.1 | 18 |
| 97FMO1728-07* | 4.3 | 22 | 10.9 | 21 | 17.5 | 20 |
| 97FMO1817-01 | 5.3 | 23 | 12.0 | 22 | 19.5 | 22 |
| 97FMO1822-01 | 4.3 | 20 | 10.5 | 21 | 17.4 | 21 |
| 97FMO2017-01 | 2.5 | 16 | 8.1 | 18 | 15.3 | 18 |
| 97FMO2222-01 | 4.8 | 24 | 9.5 | 24 | 15.9 | 24 |
| 97FMO1617-07 | 4.1 | 19 | 11.5 | 21 | 18.3 | 20 |
| Huaza. No. 3 (CK3) | 3.9 | 21 | 8.9 | 20 | 15.6 | 13 |
| C022 (CK4) | 3.1 | 17 | 7.2 | 20 | 11.6 | 20 |
| Huaza No. 3 (CK5) | 2.6 | 19 | 9.0 | 20 | 15.9 | 18 |
| C022 (CK6) | 2.1 | 11 | 5.7 | 15 | 12.4 | 15 |

Example 11

Expression Profiles of Lines Selected Directly for Blackleg or *Sclerotinia* Resistance As described in Example 9, lines were selected for resistance to blackleg under field conditions. Expression of the four transgenes in leaves was examined by ELISA on five of the selected lines from the T2 generation (4 analyses with 2 plants per line and two wells per sample). Table 12 provides the expression levels in leaves relative to line 213. A number of different combinations of transgene expression were observed in-lines selected for *phoma* resistance. The line strongly expressing the four transgenic PRs (line 97FM01421-01) was most resistant to *phoma* in the test on the cotyledons, indicating that glucanase, chitinase and/or PR1 may have an important role in resistance to *phoma* on the cotyledons. Line 97FM01625 was most resistant to *phoma* and *sclerotinia* in the stem test, indicating that chitinase and AP24 may play an important role in resistance to *phoma* and *sclerotinia* on the stem.

TABLE 12

| | Expression in Leaf | | | |
|---|---|---|---|---|
| | Glucanase | Chitinase | PR1 | AP24 |
| Line 213 | 100 | 100 | 43 | 100 |
| Line 205 | 0 | 0 | 0 | 0 |
| Westar | 0 | 0 | 0 | 0 |
| 97FM01421 | 68 | 75 | 75 | 237 |
| 97FM01617 | 1 | 70 | 18 | 37 |
| 97FM01822 | 1 | 0 | 0 | 274 |
| 97FM01419 | 1 | 0 | 0 | 117 |
| 97FM01625 | 1 | 32 | 0 | 151 |

Example 12

*Sclerotinia* Resistance in T6 Plants

Field tests for *sclerotinia* resistance were performed as described above (Example 10) on T6 lines. Test results are provided in Table 13. Susceptible canola variety Westar and resistant variety 5C21 were used as checks in the test. Resistant variety 5C21 was a selection from C022 (see resistant check in Example 10). Westar had a lesion size of 3.36 cm seven days after infection and a lesion size of 7.26 cm 12 days after infection. Resistant check 5C21 had a lesion size of 1.14 cm seven days after infection and a lesion size of 2.27 cm 12 days after infection, which is 34.02% and 31.23% of the lesion size of Westar at seven days and 12 days after infection, respectively.

TABLE 13

Field Test for Sclerotinia Resistance in T6 Plants

| ID | GEN | Mean Lesion Size (cm) | | Lesion Size vs. Westar (%) | | Range (cm) | |
|---|---|---|---|---|---|---|---|
| | | 7 days | 12 days | 7 days | 12 days | 7 days | 12 days |
| 97FMO1625-08 | T6 | 0.58 | 1.41 | 17.37 | 19.48 | 0.00–1.24 | 0.61–2.74 |
| 97FMO1625-03 | T6 | 0.54 | 1.49 | 15.98 | 20.49 | 0.15–0.92 | 0.67–2.94 |
| 97FMO01913-02 | T6 | 1.01 | 1.60 | 30.20 | 22.01 | 0.62–1.58 | 1.11–2.01 |
| 5C21 | | 1.14 | 2.27 | 34.02 | 31.23 | 0.51–1.75 | 0.85–5.74 |
| 97FM00932-09 | T6 | 1.47 | 3.07 | 43.75 | 42.31 | 1.06–2.14 | 1.18–4.41 |
| 97MO01617-01 | T6 | 1.32 | 3.26 | 39.41 | 44.93 | 0.35–1.75 | 0.71–4.61 |
| 97FMO1625-01 | T6 | 1.48 | 3.93 | 44.02 | 54.19 | 0.54–2.71 | 1.39–5.84 |
| 97FMO01913-02 | T6 | 1.27 | 4.63 | 37.70 | 63.77 | 0.21–2.13 | 2.25–6.51 |
| 97FMO1728-01 | T6 | 2.16 | 4.74 | 64.16 | 65.29 | 1.04–3.68 | 1.08–8.58 |
| 97FMO1617-01 | T6 | 1.93 | 5.20 | 57.36 | 71.57 | 1.12–2.95 | 2.64–7.92 |
| Westar | | 3.36 | 7.26 | 100.00 | 100.00 | 2.25–4.50 | 5.96–8.03 |

All the lines in the test showed better resistance to *sclerotinia* disease than Westar. Lines were classified as resistant to disease when lesion size of the line was 30% of the lesion size of Westar, moderately resistant to disease when lesion size of the line was 30%–50% of the lesion size of Westar, moderately susceptible to disease when lesion size of the line was 50%–75% of the lesion size of Westar, and highly susceptible to disease when lesion size of the line was 75%–100% of the lesion size of Westar.

The following lines showed substantial *sclerotinia* resistance improvement over Westar: line 97FM01625-08, line 97FM01625-03, and line 97FM01913-02. Line 97FM01625-08 had a lesion size of 0.58 cm 7 days after infection (17.37% of Westar lesion size) and 1.41 cm 12 days after infection (19.48% of Westar lesion size). This line also exhibited improved blackleg resistance over Westar in earlier trials. Line 97FM01625-03 was one of the most resistant lines in earlier trials. It was consistently resistant to sclerotinia, with an average lesion size of 0.54 cm 7 days after infection (15.98% of Westar lesion size) and 1.49 cm 12 days after infection (20.49% of Westar lesion size). Line 97FM01913-02 had a lesion size of 1.01 cm 7 days after infection (30.2% of Westar lesion size) and 1.60 cm 12 days after infection (22.01% of Westar lesion size). This line also exhibits improved blackleg resistance over Westar.

Lines 97FM00932-09, 97FM001617-01, and 97FM001625-01 each were classified as moderately resistant with lesion sizes 30–50% of that of Westar at both 7 and 12 days after infections. These lines also exhibited blackleg resistance.

Lines 97FM01913-02, 97FM01728-01 and 97FM01617-01 exhibited resistance that was slightly improved over Westar, with lesion sizes 50–75% of that of Westar at both 7 and 12 days after infection.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A transgenic plant comprising at least one nucleic acid construct, wherein said at least one construct comprises a) a regulatory element operably linked to a nucleic arid encoding a chitinase polypeptide; b) a regulatory clement operably linked to a nucleic acid encoding a β-1,3-glucanase polypeptide; c) a regulatory element operably linked to a nucleic acid encoding an osmotin polypeptide; and d) a regulatory element operably linked to a nucleic acid encoding a pathoenesis-related (PR1) polvi,einide, wherein said transgenic plant is resistant to *Sclerotinia* relative to a conesponding control plant.

2. The transgenic plant of claim 1, wherein said plant is a Cruciferae plant.

3. The transgenic plant of claim 1, wherein said plant is selected from the group consisting of *Brassica napus, Brasstca juncea, Brassica nigra, Brassica oleracae, Brassica carinata* and *Brassica rapa*.

4. The transgenic plant of claim 1, wherein said plant is *Helianthus annuus*.

5. The transgenic plant of claim 1, wherein said PR1 polypeptide is intraceilularly expressed.

6. The tranagenic plant of claim 1, wherein said PR1 polypeptide is from tobacco, parsley, *Brassica napus*, or *Arabidopsis thaliana*.

7. The tranagenic plant of claim 1, wherein said chitinase polypeptide is from tobacco, bean, cucumber, tomato, *Arabidopsis thaliana*, or bacteria.

8. The transgenic plant of claim 7, wherein said chitinase polypeptide is intracellularly expressed.

9. The transgenic plant of claim 1, wherein said β-1,3-glucanase polypeptide is from pea, soybean, tobacco, bean, rice, cucumber, or tomato.

10. The transgenic plant of claim 9, wherein said β-1,3-glucanase polypeptide is intracellularly expressed.

11. The tranagenic plant of claim 1, wherein said osmotin polypeptide is from tobacco, soybean, carrot, cotton, potato, or bean.

12. The tranagenic plant of claim 1, wherein said chitinase, β-1,3-glucanase, and osmotin polypeptides are constitutively expressed in the stem of said transgenic plant.

13. The transgenic plant of claim 1, wherein said chitinase, β-1,3-glucauase, and osrnotin polypeptides are constitutively expressed in leaves of said transgenic plant.

14. The transgenic plant of claim 1, wherein said transgenic plant is resistant to *Scierotinia* on the stem.

15. The transgenic plant of claim 1, wherein said transgenic plant is resistant to *Scierotinia* on the leaves.

16. A transgenic plant comprising four nucleic acid constructs, each said construct comprising a regulatory element operably linked to a nucleic acid encoding different polypeptide, wherein one polypeptide is an osmotin, one is a PR1 polypeptide, one is a β-1,3-glucanase, and one is a chitinase.

17. A method of producing a *Brassica* plant line resistant to *Phoma lingam*, said method comprising
   a) introducing at least one nucleic acid construct into cells of a *Brassica* species that is susceptible to *Phoma lingam*, wherein said nucleic acid construct comprises i) a regulatory element operably linked to a nucleic acid encoding an osmotin polypeptide; ii) a regulatory element operably linked to a nucleic acid encoding a chitinase polypeptide; iii) a regulatory element operably linked to a nucleic acid encoding a β-1,3-glucanase polypeptide: and iv) a regulatory element operably linked to a nucleic acid encoding a PR1 polypeptide;
   b) obtaining one or more progeny plants from said cells;
   c) identifying at least one of said progeny plants that is resistant to *Phoma lingam*; and
   d) producing said plant line from said at least one progeny plant by self- or cross-pollination, wherein said plant line is resistant to *Phoma lingam*.

18. The method of claim 17, wherein said *Brassica* species is *B. napus*.

19. The method of claim 17, wherein said *Brassica* species is *B. rape*.

20. The method of claim 17, wherein said *Brassica* species is *B. juncea*.

21. The method of claim 17, wherein said *Brassica* species is *B. nigra, B. cariata*, or *B. oleracea*.

22. A method of producing a plant line resistant to *S. sclerotiorum*, said method comprising
   a) introducing at least one nucleic acid construct into cells of a plant species that is susceptible to *S. sclerotiorum*, wherein said nucleic acid construct comprises i) a regulatory element operably linked to a nucleic acid encoding a chitinase polypeptide; ii) a regulatory element operably linked to a nucleic acid encoding a β-1,3-glucanase polypepride; iii) a regulatory element operably linked to a nucleic acid encoding an osmotin polypeptide; and iv) a regulatory element operably linked to a nucleic acid encoding a PR1 polypeptide;
   b) obtaining one or more progeny plants from said cells;
   c) identing at least one of said progeny plants that is resistant to *S. sclerotiorum*; and
   d) producing said plant line from said at least one progeny plant by self- or cross-pollination, wherein said plant line is resistant to *S. sclerotiorum*.

23. The method of claim 22, wherein said plant species that is susceptible to *S. sclerotiorum* is a Cruciferae plant.

24. The method of claim 23, wherein said Cruciferae plant is a *Brassica* plant.

25. The method of claim 22, wherein said plant species that is susceptible to *S. sclerotiorum* is soybean.

26. The method of claim 22, wherein said plant species that is susceptible to *S. sclerotiorum* is *Helianthus annuus*.

27. The method of claim 22, wherein said plant species that is susceptible to *S. sclerotiorum* is tomato.

* * * * *

UNITED STATES PATENT AND TRADEMARK OFFICE
CERTIFICATE OF CORRECTION

PATENT NO.        : 7,141,723 B2
APPLICATION NO. : 10/470427
DATED             : November 28, 2006
INVENTOR(S)       : Zhizheng Chen, Sonia Hallier and Xinmin Deng It is certified that error appears in the above-identified patent and that said Letters Patent is hereby corrected as shown below:

Column 27, lines 41-42, please delete "pathoenesis" and insert --pathogenesis--therefor;

Column 27, line 42, please delete "polvi,einide" and insert --polypeptide--therefor;

Column 27, line 43, please delete "conesponding" and insert --corresponding--therefor;

Column 27, line 49, please delete "Brasstca" and insert --Brassica--therefor;

Column 27, line 54, please delete "intraceilularly" and insert --intracellularly--therefor;

Column 27, line 55, please delete "tranagenic" and insert --transgenic--therefor;

Column 27, line 58, please delete "tranagenic" and insert --transgenic--therefor;

Column 28, line 1, please delete "tranagenic" and insert --transgenic--therefor;

Column 28, line 4, please delete "tranagenic" and insert --transgenic--therefor;

Column 28, line 8, please delete "glucauase" and insert --glucanase--therefor;

Column 28, line 8, please delete "osrnotin" and insert --osmotin--therefor;

Column 28, line 11, please delete "Scierotinia" and insert --Sclerotinia--therefor;

Column 28, line 13, please delete "Scierotinia" and insert --Sclerotinia--therefor;

Column 28, line 41, please delete "rape" and insert --rapa--therefor;

Column 28, line 45, please delete "cariata" and insert --carinata--therefor;

Column 28, line 54, please delete "polypepride" and insert --polypeptide--therefor;

UNITED STATES PATENT AND TRADEMARK OFFICE
CERTIFICATE OF CORRECTION

PATENT NO. : 7,141,723 B2
APPLICATION NO. : 10/470427
DATED : November 28, 2006
INVENTOR(S) : Zhizheng Chen, Sonia Hallier and Xinmin Deng It is certified that error appears in the above-identified patent and that said Letters Patent is hereby corrected as shown below:

Column 28, line 59, please delete "identing" and insert --identifying--therefor.

Signed and Sealed this

First Day of May, 2007

JON W. DUDAS
*Director of the United States Patent and Trademark Office*